United States Patent [19]
Comfort

[11] Patent Number: 6,143,036
[45] Date of Patent: Nov. 7, 2000

[54] BONE AUGMENTATION FOR PROSTHETIC IMPLANTS AND THE LIKE

[75] Inventor: Christopher J. Comfort, Sunnyvale, Calif.

[73] Assignee: Comfort BioMedical, Inc., Sunnyvale, Calif.

[21] Appl. No.: 09/236,164

[22] Filed: Jan. 22, 1999

Related U.S. Application Data

[62] Division of application No. 08/993,945, Dec. 18, 1997.

[51] Int. Cl.$^7$ .................................................. A61F 2/28
[52] U.S. Cl. ............................. 623/23.54; 623/23.49; 623/23.57
[58] Field of Search ................ 623/16, 18; 606/76, 606/77; 433/173, 175, 201.1

[56] References Cited

U.S. PATENT DOCUMENTS

| | | |
|---|---|---|
| 3,894,297 | 7/1975 | Mittelmeier et al. . |
| 3,905,777 | 9/1975 | Lacroix . |
| 3,906,550 | 9/1975 | Rostoker et al. . |
| 4,064,567 | 12/1977 | Burstein et al. . |
| 4,199,824 | 4/1980 | Niederer . |
| 4,261,063 | 4/1981 | Blanquaert . |
| 4,309,488 | 1/1982 | Heide et al. . |
| 4,394,370 | 7/1983 | Jefferies . |
| 4,430,761 | 2/1984 | Niederer et al. . |
| 4,472,840 | 9/1984 | Jefferies . |
| 4,479,271 | 10/1984 | Bolesky et al. . |
| 4,483,678 | 11/1984 | Nishio et al. . |
| 4,526,909 | 7/1985 | Urist . |
| 4,530,116 | 7/1985 | Frey . |
| 4,535,487 | 8/1985 | Esper et al. . |
| 4,536,894 | 8/1985 | Galante et al. . |
| 4,549,319 | 10/1985 | Meyer . |
| 4,563,489 | 1/1986 | Urist . |
| 4,570,271 | 2/1986 | Sump . |
| 4,589,883 | 5/1986 | Kenna . |
| 4,608,053 | 8/1986 | Keller . |
| 4,636,219 | 1/1987 | Pratt et al. . |
| 4,660,755 | 4/1987 | Farling et al. . |
| 4,693,721 | 9/1987 | Ducheyne . |
| 4,795,472 | 1/1989 | Crowninshield et al. . |
| 4,829,152 | 5/1989 | Rostoker et al. . |
| 4,846,837 | 7/1989 | Kurze . |
| 4,923,513 | 5/1990 | Ducheyne et al. . |
| 4,960,646 | 10/1990 | Shimamune et al. . |
| 5,013,649 | 5/1991 | Wang et al. . |
| 5,018,285 | 5/1991 | Zolman et al. . |

(List continued on next page.)

OTHER PUBLICATIONS

Brian J. Cole, et al.; "Use of Bone Morphogenetic Protein 2 on Ectopic Porous Coated Implants in the Rat"; Clinical Orthopaedics and Related Research No. 345; 1997 Lippincott–Raven Publishers; pp. 219–228.

Kevin A. Thomas; "Hydroxyapatite Coatings"; Mar. 1994, Orthopedics; vol. 17 No. 3; pp. 267–278.

David J. Baylink, et al.; "Growth Factors to Stimulate Bone Formation"; 1993, Journal of Bone and Mineral Reseach vol. 8 No. 3; pp. S565–S572.

Stephen D. Cook, et al.; "Hydroxyapatite–Coated Titanium for Orthopedic Implant Applications"; Clinical Orthopaedics and Related Research; Jul. 1998, No. 232; pp. 225–243.

R.J.B. Sakkers, et al.; "Assessment of Bioactivity for Orthopedic Coatings in a Gap–Healing Model"; 1997 John Wiley & Sons, Inc.; pgs. 265–273.

*Primary Examiner*—David H. Willse
*Attorney, Agent, or Firm*—Blakely, Sokoloff, Taylor & Zafman, LLP

[57] ABSTRACT

Bone augmentation in a mammalian body by insertion of a mesh comprising one or more fibrillar wires having a coating into a bone cavity or socket. The one or more fibrillar wires are arranged or assembled into a woolly structure, which may be infused or cultured with a bone morphogenic protein. The mesh is sealed in the cavity to permit new bone to form over time, resulting in an osteointegrated matrix of bone reinforced by the fibrillar wires of the mesh.

12 Claims, 4 Drawing Sheets

U.S. PATENT DOCUMENTS

| | | |
|---|---|---|
| 5,030,233 | 7/1991 | Ducheyne . |
| 5,236,456 | 8/1993 | O'Leary et al. . |
| 5,344,457 | 9/1994 | Pilliar et al. . |
| 5,344,654 | 9/1994 | Rueger et al. . |
| 5,360,446 | 11/1994 | Kennedy . |
| 5,366,508 | 11/1994 | Brekke . |
| 5,373,621 | 12/1994 | Ducheyne et al. . |
| 5,458,653 | 10/1995 | Davidson . |
| 5,466,259 | 11/1995 | Durette ................................. 623/4 |
| 5,597,897 | 1/1997 | Ron et al. . |
| 5,606,019 | 2/1997 | Cappello . |
| 5,609,633 | 3/1997 | Kokubo ................................. 623/16 |
| 5,609,635 | 3/1997 | Michelson . |
| 5,629,009 | 5/1997 | Laurencin et al. . |
| 5,635,373 | 6/1997 | Wozney et al. . |
| 5,639,237 | 6/1997 | Fontenot . |
| 5,645,591 | 7/1997 | Kuberasampath et al. . |
| 5,652,118 | 7/1997 | Ozkaynak et al. . |
| 5,658,333 | 8/1997 | Kelman et al. . |
| 5,683,459 | 11/1997 | Brekke . |
| 5,707,962 | 1/1998 | Chen et al. . |
| 5,714,589 | 2/1998 | Oppermann et al. . |
| 5,733,564 | 3/1998 | Lehtinen . |

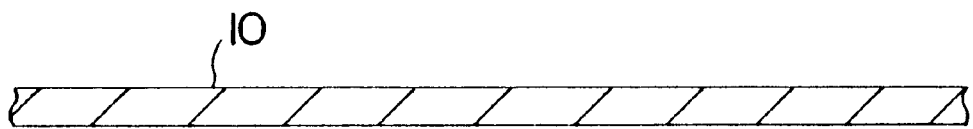
FIG. IA
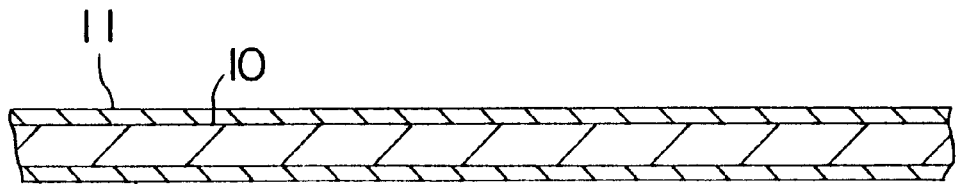
FIG. IB
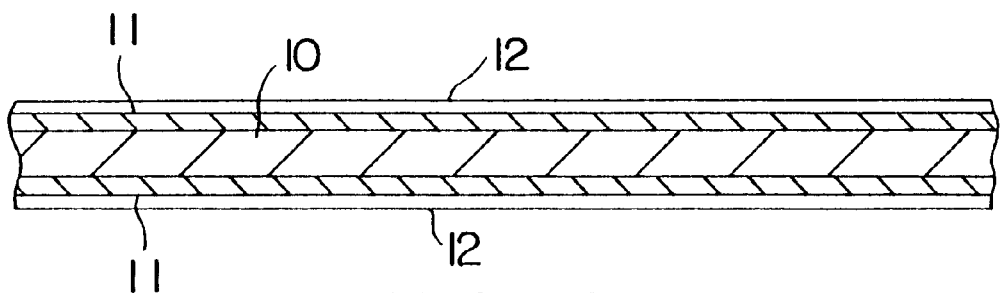
FIG. IC
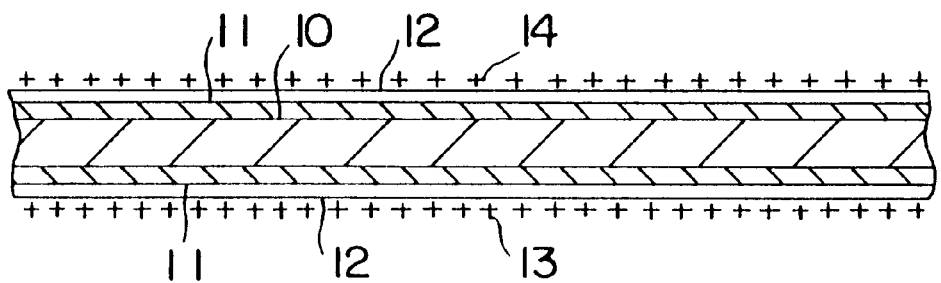
FIG. ID

BONE AUGMENTATION FOR PROSTHETIC IMPLANTS AND THE LIKE

This patent application is a Divisional of U.S. patent application Ser. No. 08/993,945 filed Dec. 18, 1997.

FIELD OF THE INVENTION

The present invention relates generally to the field of regeneration of skeletal tissues; more specifically, to devices and methods for inducing osteogenic bone growth in skeletal areas supporting a prosthetic implant or in need of reconstructive repair.

BACKGROUND OF THE INVENTION

The use of prosthetic implants for replacing or supplementing fractured, damaged, or degenerated skeletal bone in a mammalian body is commonplace in the medical arts. Usually, the prosthetic implant device is made of a biocompatible metal such as stainless steel, cobalt-chromium-molybdenum alloy, tungsten, titanium, cobalt-chromium-tungsten-nickel, and similar alloys. Most often, the prosthetic implant device is intended to become a permanent part of the skeletal structure.

One well-known technique for permanently attaching a metallic prosthesis to an adjoining bone or bones is to secure the implant in place with a polymethyl-methacrylate cement. By way of example, U.S. Pat. No. 5,360,146 describes a method of manufacturing prosthetic implant devices that may be secured into human bodies in this manner.

One of the problems that occur in implant devices is the gradual loosening of the prosthesis from the bone over time. This problem is especially prevalent where the prosthesis is subject to large functional loads and sheer stresses. Crania-facial implants, which are commonly used in the reconstruction or replacement of single teeth, are particularly prone to this problem. For instance, the difficulty in achieving a dental prosthesis that is strongly bonded to maxillary and mandibular bone, and which can withstand large sheer and tensile stress loads, has lead to the development of a variety of attachment mechanisms. Many of these mechanisms attempt to adaptively reform bone around the prosthesis, with the newly formed bone eventually bonding to the outer surface of the implant.

A variety of methods for promoting bone formation and attachment have been proposed. For example, U.S. Pat. No. 5,639,237 describes an endosseous dental implant having a dimpled surface texture for use in prosthetic reconstruction of crania-facial bones. The indented surface increases the surface area for bone proliferation, thereby enhancing the mechanical fixation/anchoring strength of the dental implant as compared to ordinary dental implants having a similar geometry.

Other approaches have attempted to strengthen the attachment of the bone at the site of the implantation. One such method is taught in U.S. Pat. No. 5,344,654, which claims that a strong bond is achieved between existing bone and the prosthesis by coating the prosthetic device with an osteogenic protein. To enhance endochondral bone formation, U.S. Pat. No. 5,656,450 teaches compositions and methods for effecting wound healing, specifically the activation of latent growth factor through matrix vesicles. Biodegradable polymeric implants are described which may be prepared containing latent growth factor, matrix vesicles, or matrix vesicle extract. An osteogenic device capable of inducing the formation of endochondral bone when implanted in the mammalian body is also disclosed in U.S. Pat. No. 5,645,591. This device includes an osteogenic protein dispersed within a porous matrix comprising a polymer of collagen and glycosaminoglycan.

Yet another approach for improving the strength and stability of a dental implant is discussed in U.S. Pat. No. 5,383,935. According to the teachings of this patent, a prosthetic device for implantation into skeletal bone generates current flow for calcium phosphate mineral formation between the implant and the surrounding bone. The formation of calcium phosphate minerals at the implant-bone interface is described as encouraging bone attachment to the implant, thereby providing stronger fixation of the implant into the skeletal structure.

An altogether different technique for enhancing bone density at the region of the implant is described in U.S. Pat. No. 5,344,457. This reference teaches effectively transferring loading stress from a dental implant to the surrounding bone through the use of an implant having a tapered body shape. Application of a vertical force on the tapered implant produces a sheer force component in addition to the normal force component acting on the surrounding bone.

Despite the plethora of prior art approaches for securing an implanted structure into mammalian bone, failures still occur. These failures are primarily due to the inability of the non-cortical bone to support the load of the implant. The reason why is because the new bone growth surrounding the implant surface is usually weaker, or more porous, as compared to the cortical areas of bone. Since internal areas of bone tend to be softer, more porous, and less dense than outer, circumferential regions of bone, implants into these areas are prone to failure due to movement and a lack of surrounding bone structure. This is particularly true in the case of dental implants into the maxilla and mandible.

Thus, there is a need in the medical and dental arts for improving the strength and integrity of the bone that surrounds and attaches to a prosthetic implant device. As will be seen, the present invention provides a method and a structure for increasing the load bearing strength of the bone surrounding an prosthesis. In addition, the present invention provides a novel way to augment both endo and exo bone formation for a variety of applications.

SUMMARY OF THE INVENTION

Bone augmentation in a mammalian body is described. A primary application of the present invention is to support a prosthetic implant device. In one embodiment, a method is provided for enhancing the mechanical strength of the prosthesis by reinforcement of bone in the region surrounding the implant device.

The method includes the step of inserting a mesh into a bone cavity or socket. The mesh comprises one or more fibrillar wires having a hydroxy appetite coating. The one or more fibrillar wires are arranged or assembled into a woolly structure. In addition, the mesh may be infused, incubated, or cultured with a bone morphogenic protein, which coats the one or more wires. After insertion, the mesh is sealed in the cavity. This permits new bone to grow into the mesh-filled cavity. Over time, an osteointegrated matrix of bone reinforced by the fibrillar wires of the mesh is formed.

Once adequate bone growth has occurred, the osteointegrated structure may be cored or otherwise shaped to create an opening, which accommodates the implant device. The prosthetic implant device is then securely inserted into the opening. The resulting implant structure is characterized by enhanced fixation/anchoring strength of the implant due to the reinforced nature of the surrounding bone, which has improved multidirectional stress loading support capability.

BRIEF DESCRIPTION OF THE DRAWINGS

The present invention will be understood more fully from the detailed description which follows and from the accompanying drawings, which, however, should not be taken to limit the invention to the specific embodiments shown, but rather are for explanation and understanding only.

FIGS. 1A–1D illustrate various steps involved in the preparation of a filamentous wire in accordance with one embodiment of the present invention.

DETAILED DESCRIPTION

Figure 2:
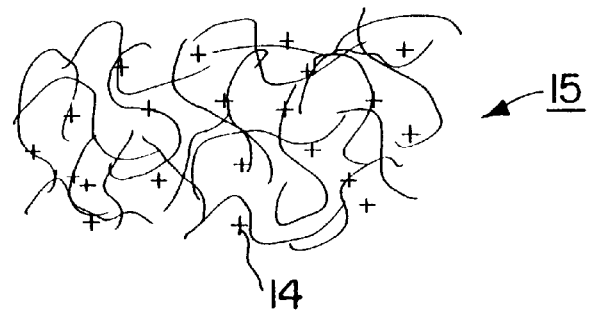
FIG. 2 is a conceptual illustration of mesh utilized for in vivo bone augmentation according to one aspect of the present invention.

The present invention provides a technique for augmenting bone growth that is particularly well suited for enhanced support of a prosthetic implant device. In the following description, numerous specific details are set forth, such as material types, dimensions, specific tissues, etc., in order to provide a thorough understanding of the present invention. Practitioners having ordinary skill in the biomedical arts will understand that the invention may be practiced without many of these details. In other instances, well-known devices, methods, and biochemical processes have not been described in detail to avoid obscuring the invention.

As explained previously, inert implanted materials formed into various structures have been used to replace bone and bone functions in mammalian subjects. The implanted structure, which usually comprises material such a stainless steel, titanium alloys, or chromium-cobalt alloys are typically cemented or screwed into place in the bone using a number of compounds that are well known in the prior art. In addition, the surface of the prosthetic implant structure may be roughened to improve bone attachment to the metal prosthesis. Administrating diphosphonates subcutaneously to obtain a cement-less prosthesis may further enhance bone growth onto the implanted material.

One of the primary modes of failure of prosthetic implants is the inability of the surrounding bone to support the load of the implant. This is especially true in areas that are weaker due to the softer, porous, less dense, or spongier nature of the bone. In particular, dental implants are prone to fail due to movement of the prosthesis together with lack of a rigid surrounding bone structure.

The present invention offers a solution to the foregoing problems by providing a mesh that may be placed into a cavity of a bone to enhance the structural integrity of the bone itself. According to one embodiment, the mesh comprises one or more fibrillar wires arranged in a random, woolly structure. After inserting the mesh into a cavity of a bone, fibroblast/osteoblast infiltration occurs such that new bone growth fills the internal cavity.

An important aspect of the present invention is that the new bone growth is integrated with the woolly structure. The one or more wires of the mesh function as reinforcing rods that provide multidirectional strength to the newly formed bone. Structurally reinforcing the bone in this manner means that the bone that supports and stabilizes the implant device is capable of distributing the physical forces of the implant over a large internal surface area. The result is a more structurally secure prosthetic implant that can withstand greater exerted stress forces. This highly beneficial feature makes the present invention ideally suited for improving the strength and fixation of dental implant devices, or any device implanted into the center of bone.

With reference now to FIGS. 1A–1D, various steps in the preparation of the one or more filamentous wires utilized in accordance with one embodiment in the present invention are illustrated. FIG. 1A shows a portion of a filamentous or fibrillar wire 10 that comprises a metal such as titanium, tantalum, gold, stainless steel, or other inert, implantable alloys that may be manufactured in a thread-like form. In one embodiment, ordinary titanium wire is utilized having a preferred thickness in the range of approximately 100–300 microns. Of course, other thickness' may also be used.

Additionally, the shape of wire 10 may have a cross-section that is elliptical, rectilinear, round, etc. In other words, the precise shape of the wire is not considered essential to the present invention. The purpose of the wire (or multiple wire strands) is to provide sufficient surface area for the bone to attach to, and also strengthen, the associated bone matrix. This is achieved by arranging or assembling the wire or wires into a woolly structure. The arrangement of the wire in the woolly structure may be entirely random or may consist of a fabric having a more regular pattern. For example, conventional manufacturing methods for commercial-grade steel wool are considered acceptable for producing the mesh of the present invention.

FIG. 1B illustrates a cross-sectional portion of wire 10 having an oxide coating 11 that covers the outer surface of the wire. In the case where wire 10 comprises titanium, the oxide layer obviously comprises a titanium oxide which may be formed according to ordinary methods. The titanium oxide is grown to a thickness in the range of 3–5 nm thick.

Following oxide layer formation, or simultaneous therewith, the wire may be sterilized through plasma oxidation, plasma cleaning and/or autoclaving. Once wire 10 has been oxidized and sterilized, the wire is then coated with a synthetic bone material, e.g., a hydroxy appetite. FIG. 1C shows a hydroxy appetite layer 12 coating the oxide layer 11 which has been grown around wire 10. The application of the hydroxy appetite coating may be performed according to conventional methods. However, because wire 10 will be subjected to subsequent bending and twisting forces, hydroxy appetite coating 12 should be diffusely applied. In other words, if hydroxy appetite coating 12 is applied to thickly, cracking and breakage may occur due to the crystalline nature of the hydroxy appetite itself. Diffusely coating of wire 10 with hydroxy appetite coating 12 therefore allows the wire to be randomly bent and matted into a mesh 15.

FIG. 1D illustrates a bone morphogenic protein (BMP) coating 14 that has been formed or cultured over hydroxy appetite coating 12. In one embodiment, BMP coating 14 comprises a protein substance that is applied to the one or more wires 10 prior to formation of mesh 15. For example, the protein known as BMP_5 or BMP_7 with collagen, which Creative Biomedical, Inc. commercially produces, may be utilized. A variety of different types of collagen may be used, including type_4 collagen or type_2 collagen. Alternatively, heparin may be employed as a carrier instead of collagen.

In another embodiment, the woolly mesh may be formed first from a single length of wire (or multiple wire strands), with the BMP then being infused into the porous mesh.

FIG. 2 shows the wooly structure of mesh 15. In the embodiment of FIG. 2, mesh 15 comprises a fibrillar titanium wire that has been infused with a collagen bone morphogenic protein base. This base forms coating 14 over the wire. It is appreciated that BMP coating 14 may comprise other matrix proteins. Fibrinogen, a-thrombin, FGH, as well as other various antibiotics, growth hormones, gene therapies, or combinations of these factors may also be utilized to promote healthy bone growth. The BMP coating 14 may be applied as a liquid or viscous gel substance that coats or is cultured onto wire 10. Incubating wire 10 with the BMP and collagen together may alternatively form coating 14.

It should be understood that the density of mesh 15 should not be so low (i.e., porous) so as to provide an inadequate support matrix for enhancing the strength of the bone which is intended to supporting the implant device. On the other hand, if mesh 15 were formed to a very high density, fibroblast/osteoblast infiltration into the mesh would be inhibited. Therefore, mesh 15 should be formed of a woolly structure having sufficient porosity so as to allow infusion of a collagen morphogenic protein base so as to facilitate dense, fibrillar infiltrate of the augmented bone growth. At the same time, the density of mesh 15 should not be so high as to inhibit fibroblast/osteoblast infiltration into the mesh.

FIGS. 3A–3D show various stages of one particular application of mesh 15 according to the present invention. By way of example, this sequence of drawings shows implantation of prosthesis 25 into bone 20. The implant device may comprise a dental implant of a type that is commonly used today.

Figure 3A:
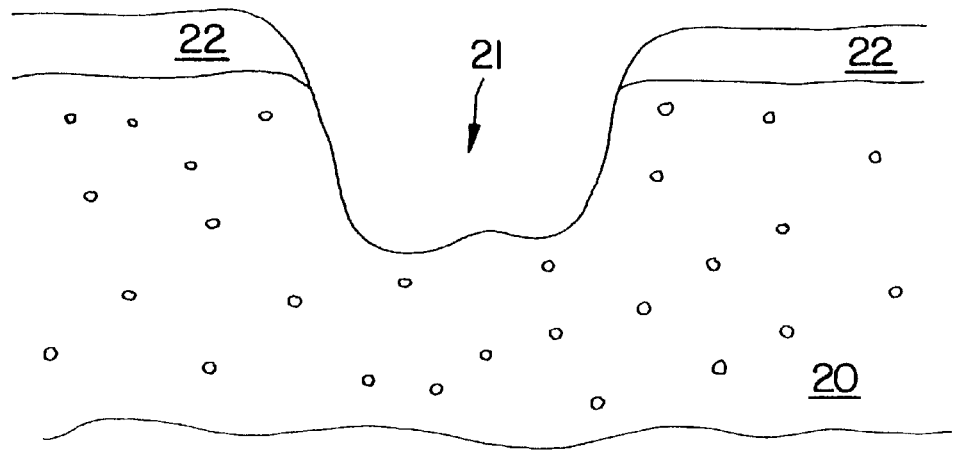
FIGS. 3A–D illustrates various steps involved in a dental root implant procedure providing enhanced fixation and support strength according to the present invention.

Beginning with FIG. 3A there is shown a cross-section of bone 20 having an opening or cavity 21 surrounded by an epithelial tissue layer 22. In the case of a dental implant, cavity 21 may represent the space created by avulsion of the natural tooth previously occupying that space. In other applications, cavity 21 may be created by the removal of either damaged or healthy bone in order to provide an attachment site for the implant device.

Figure 3B:
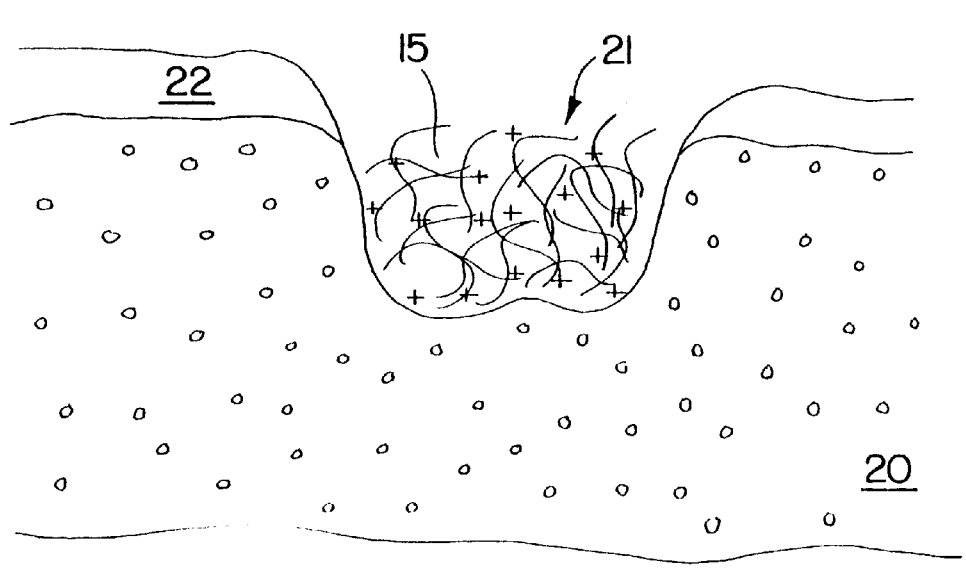

FIG. 3B shows the cross-section of FIG. 3A following insertion of mesh 15 into cavity 21. Prior to inserting mesh 15 into cavity 21, the cavity is cleaned and may be shaped utilizing conventional methods. Likewise, mesh 15 may be shaped to conform to the size of bone cavity 21. As explained above, cavity 21 may be created by the removal of a natural tooth. In other instances, cavity 21 may result from the defect of a long bone created, for example, by debritement of a dysplasila.

Figure 3C:
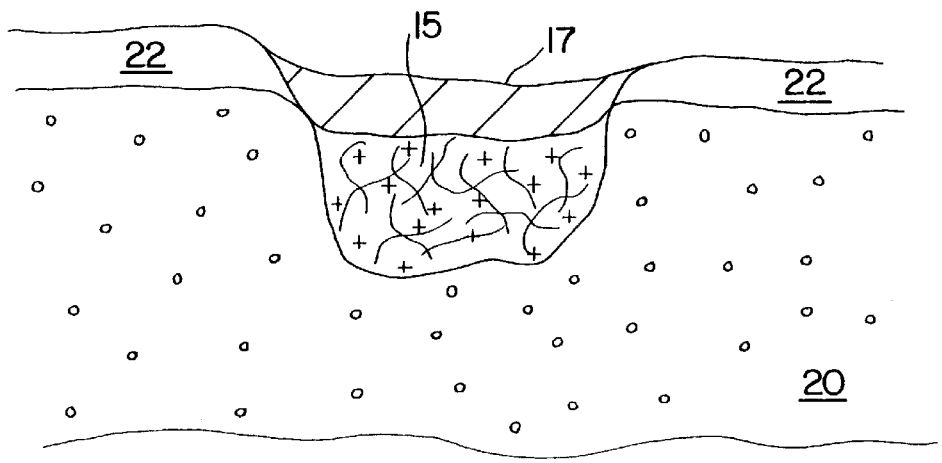

The next step in the process of bone augmentation is shown in FIG. 3C, where barrier membrane 17 is used to seal mesh 15 within the bone cavity. Ideally, barrier membrane 17 seals mesh 15 within the bone cavity to prevent epithelia attachment of outer tissue layer 22 to mesh 15. Without a suitable barrier membrane, mucosal attachment will extend into mesh 15, thereby inhibiting bone growth. By sealing off the mesh within the cavity, this type of mucosal attachment or soft tissue growth is prevented; instead osteointegration of new bone growth to the strands of mesh 15 is permitted to occur. Membrane 17 may comprise a bio-absorbable polymer the permits bone growth into mesh 15. Non-absorbable material such Gortex™ may also be used. In some cases it may be desirable to reinforce the barrier membrane 17 with titanium, or other medical grade materials. Ordinary thermoset resins or conventional glues may also be utilized in the formation of barrier membrane 17.

To fixable secure mesh 15 within bone cavity 21, an adhesive material may be applied to the inner wall of the cavity, and/or to the outer surface of the mesh itself. Fibron glue is a suitable adhesive material for this purpose.

Another option is to stimulate bone growth into mesh 15 by energizing the one or more wires of the mesh. For example, applying a relatively low-level electrical current such as 5–20 microamperes is sufficient to stimulate bone growth into the mesh-filled cavity. Of course, other forms of energy may also be used, such as radio wave frequencies (RF), microwaves, infrared or ultraviolet radiation, etc. By way of example, a RF probe may be utilized to energize the entire wool structure of mesh 15, thereby promoting adhesion of the mesh to the bone and stimulation of new bone growth.

An important mechanism by which the present invention promotes bone growth into mesh 15 is through the use of a BMP coating. In this respect, it should be appreciated that culturing of the BMPs onto the wire may be performed in vivo or in vitro. The BMPs induce new bone growth resembling endochondral bone formation, which is integrated with the woolly structure of the mesh. The BMPs also facilitate endogenous bone formation around the coated wire.

Figure 3D:
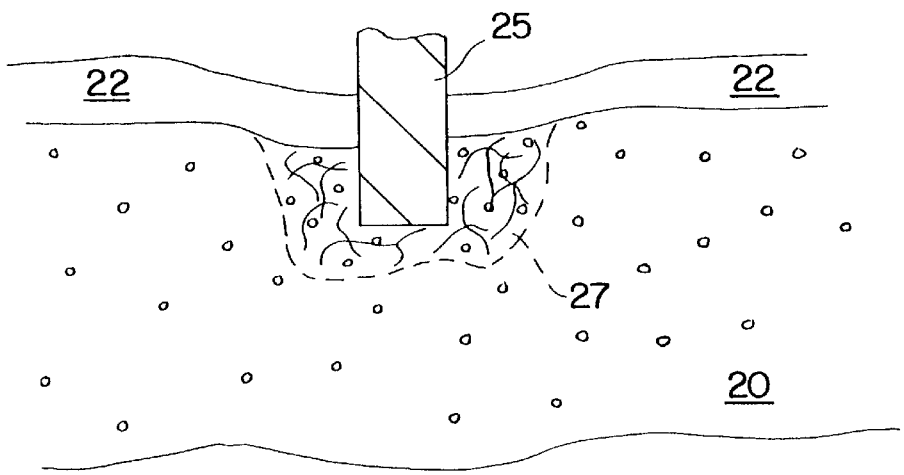

Once bone growth into the cavity is complete, the region may be cored or otherwise shaped to accept the prosthetic implant device into the bone matrix. FIG. 3D illustrates a bottom portion of an implant device 25 fixably secured/attached to bone matrix 27. Note that in FIG. 3D membrane 17 has been absorbed or dissolved, leaving tissue 22 covering the region of newly grown bone matrix 27. The osteointegrated matrix 27, consisting of new bone attached to and reinforced by mesh 15, provides improved mechanical strength and fixation for implant 25. Over time, it is expected that the bone will further integrate onto the surface layer of implant 25.

Figure 4:
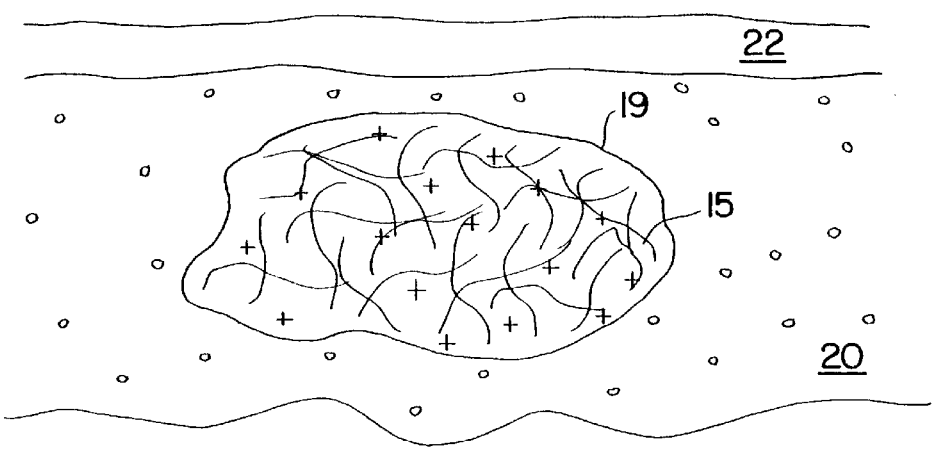
FIGS. 4 & 5 show alternative applications of the present invention in long bone or exo-bone augmentation.
Figure 5:
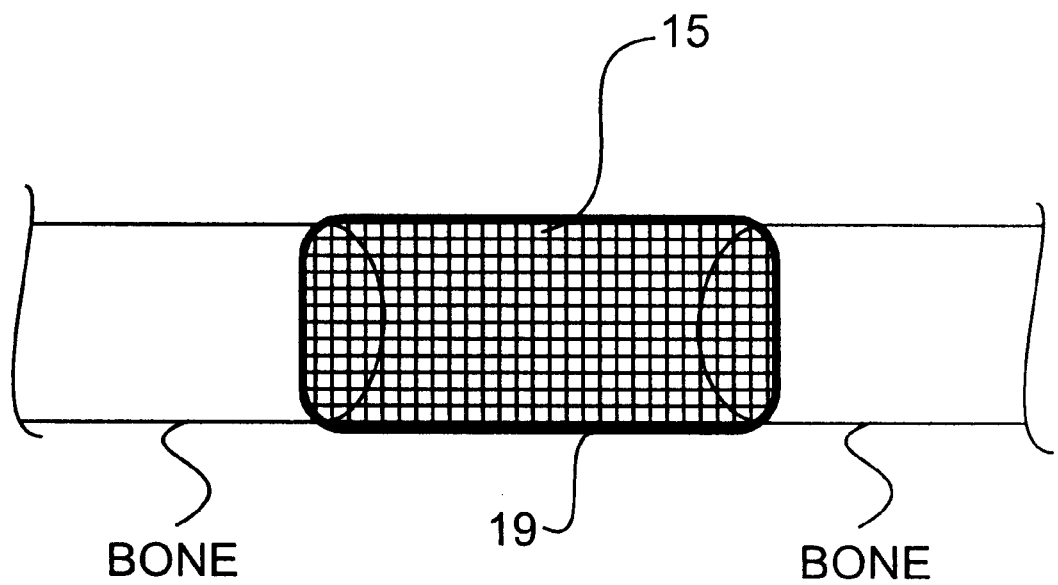

FIGS. 4 and 5 illustrate additional applications of the present invention for use in long bone or exo-augmentation. For example, this may involve the augmentation of bone onto the surface of existing skeletal bone. In this case, the wooly structure of mesh 15 may be encapsulated in a bio-absorbable polymer 19. The encapsulating material can be made from a membrane such a collagen felt, or a similarly semi-rigid material, such as polylatic acid, polyether, etc. In the case of FIG. 5, mesh 15 is woven into a more regular cross-linked pattern to provide enhanced lateral strength to the bone.

It is appreciated that the present invention is also useful in the treatment of a fractured or shattered bone. The, encapsulating material allows for bone integration at the damaged site as well as soft-tissue attachment to the surrounding soft tissue. It is appreciated that the capsule may be shaped in a variety of sizes. That is, due to its semi-rigid nature, it may be molted or adapted to fit a particular application or circumstance.

What is claimed is:

1. A method of bone augmentation to support a prosthetic implant device comprising the steps of:
   (a) inserting a mesh into a cavity of a bone, the mesh comprising one or more fibrillar wires having a hydroxy appetite coating, the one or more fibrillar wires being arranged into a woolly structure;
   (b) sealing the mesh in the cavity;
   (c) permitting the bone to grow into the cavity until an osteointegrated matrix is formed;
   (d) coring the osteointegrated matrix to create an opening; and
   (e) inserting the prosthetic implant device in the opening.

2. The method according to claim 1 further comprising the step, after step (a), of:

adhering the woolly structure to the bone with an adhesive.

3. The method according to claim 2 wherein the adhesive comprises a fibron glue.

4. The method according to claim 1 further comprising the step of: energizing the mesh so as to promote growth of the bone into the cavity.

5. The method according to claim 4 wherein the step of energizing the mesh comprises the step of:

applying an electrical current in the range of 5–25 microamperes to the mesh.

6. The method according to claim 1 wherein the one or more wires comprise a metal selected from the group consisting of titanium, tungsten, gold, and stainless steel.

7. The method according to claim 6 wherein the wires include an oxide layer.

8. The method according to claim 1 wherein the mesh is cultured with a bone morphogenic protein prior to insertion into the cavity.

9. The method according to claim 1 wherein the wires have a thickness in the range of 100 to 300 microns.

10. A method according to claim 1 wherein the hydroxy appetite coating is diffuse.

11. A method according to claim 1 wherein step (b) comprises the step of:

covering the cavity with a barrier membrane to prevent epithelial tissue attachment to the mesh.

12. The method according to claim 11 wherein the barrier membrane comprises a bio-absorbable polymer membrane.

* * * * *